United States Patent [19]

Bretscher

[11] 4,127,114
[45] Nov. 28, 1978

[54] APPARATUS FOR THE AUTOMATIC MEASUREMENT OF THE ARTERIAL PRESSURE OF A PATIENT

[75] Inventor: Max Bretscher, Niederscherli, Switzerland

[73] Assignee: Carba S.A., Liebefeld, Switzerland

[21] Appl. No.: 719,587

[22] Filed: Aug. 30, 1976

[51] Int. Cl.² ............................................. A61B 5/02
[52] U.S. Cl. ........................... 128/2.05 N; 128/2.05 M
[58] Field of Search ............... 128/2 V, 24 A, 2.05 E, 128/2.05 S, 2.05 F, 2.05 P, 2.06 R, 2.05 A, 2.05 N, 2.05 Z

[56] References Cited

U.S. PATENT DOCUMENTS

| | | | |
|---|---|---|---|
| 2,833,274 | 5/1958 | Reiss | 128/2.05 N |
| 2,865,365 | 12/1958 | Newland et al. | 128/2.05 A |
| 3,051,165 | 8/1962 | Kompelein | 128/2.05 A |
| 3,090,377 | 5/1963 | Salisbury et al. | 128/2.05 E |
| 3,137,292 | 6/1964 | Richter et al. | 128/2.05 A |
| 3,791,378 | 2/1974 | Hochberg et al. | 128/2.05 S |
| 3,841,314 | 10/1974 | Page | 128/2.05 T X |
| 3,848,582 | 11/1974 | Milani et al. | 128/2.06 R |
| 3,853,117 | 12/1974 | Murr | 128/2 V |
| 3,920,004 | 11/1975 | Nakayama | 128/2.05 A |
| 3,939,823 | 2/1976 | Kaye et al. | 128/2.05 E |
| 3,978,848 | 9/1976 | Yen et al. | 128/2.05 M |

FOREIGN PATENT DOCUMENTS 2,306,444  2/1972  Fed. Rep. of Germany ..... 128/2.05 N

OTHER PUBLICATIONS

"TTL Cookbook", by Don Lancaster, Howard Sams Company, Indianapolis, 1974, pp. 158-159.

Primary Examiner—Robert W. Michell
Assistant Examiner—Francis J. Jaworski
Attorney, Agent, or Firm—Young & Thompson

[57] ABSTRACT

This invention relates to an automatic apparatus for the measurement of the arterial pressure which comprises, within a casing, an ultrasonic emitter-receiver as well as a piezo-electric pressure detector. This casing houses also a measuring chamber partly limited at least by a supple and deformable wall intended to enter into contact with the patient.

3 Claims, 4 Drawing Figures

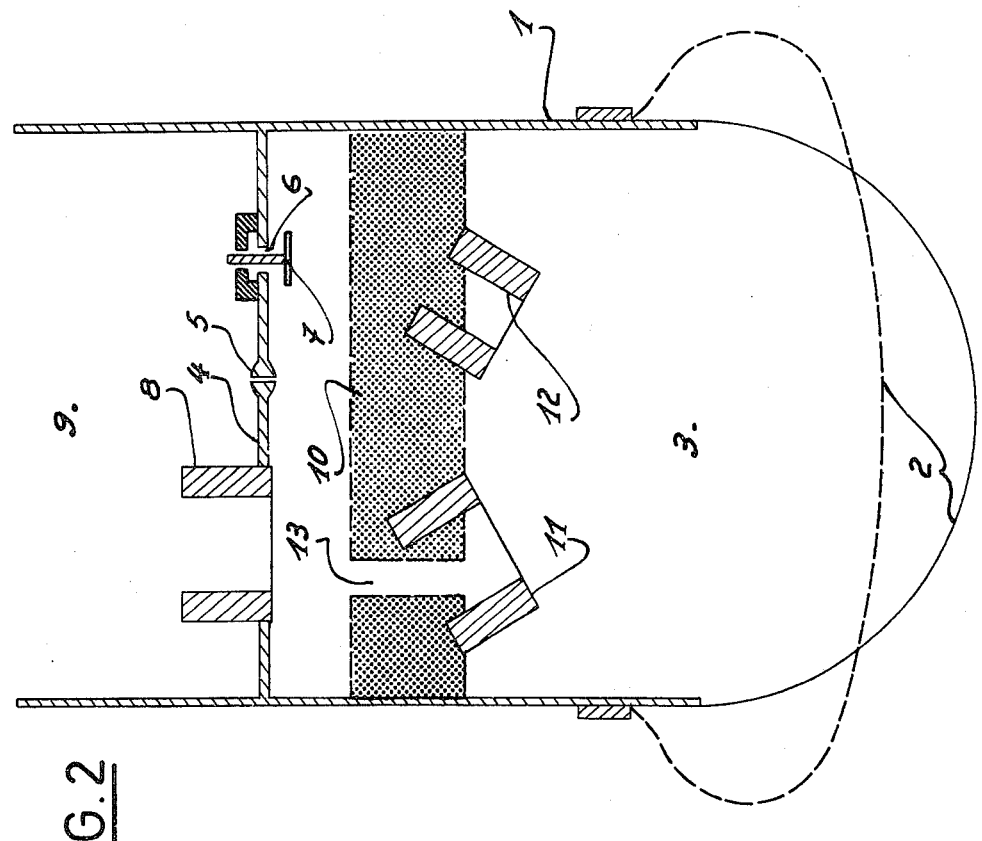
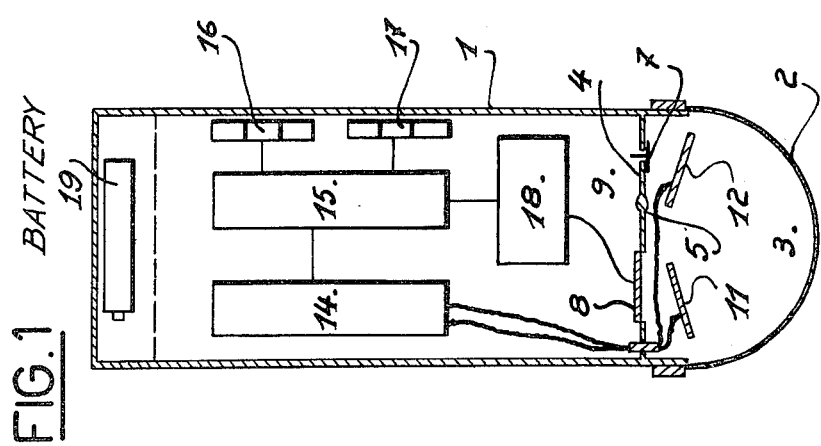

APPARATUS FOR THE AUTOMATIC MEASUREMENT OF THE ARTERIAL PRESSURE OF A PATIENT

The present invention has for its object an apparatus for the automatic measurement of the arterial pressure of a patient.

To measure this pressure by the palpation method, by the auscultative method or by the oscillometric method, one uses apparatuses which are called sphygmomanometers.

The most recent methods are based always on the principles of the sphygmomanometry but have improved means to detect the pulsations or the arterial noises. Among these methods, the most used are photoelectric plethysmography for the determination of the arterial pulsations and a system which amplifies the arterial noises.

Another detecting method for the arterial pulsations for the indirect measurement of the systolic and diastolic pressure is the use of ultrasonic waves.

The advantages of this method are its insensibility to the external noises and that it permits the measurement of the pressure even in the cases where the known methods which measure the arterial noises can not be used due to the low level of those noises (as is the case with children or hypotensive adults).

The method is based on the Doppler effect, and the frenquency variation which is obtained is:

$$dF = 2f\,v/c$$

where

F is the propagation frequency of the incident ultrasonic waves dF is the change in that frequency due to the Doppler effect f is the propagation speed of the ultrasonic waves through air v is the vibration speed of the arteria c is the propagation speed of the ultrasonic waves through the body tissues.

All these devices or methods to take the arterial pressure necessitate the use of a pneumatically inflatable bag which requires a non negligible manutention and thus a loss of time.

The aim of the present invention is to realize an automatic apparatus to measure the arterial pressure which does not use such a pneumatically inflatable bag.

The present invention has for its object an automatic apparatus for the measurement of the arterial pressure which comprises a housing, provided with a supple wall at one of its ends, having in its inside a measuring chamber partially limited by said supple wall, a piezoelectric emitter of ultrasonic waves, a piezoelectric receiver of the Doppler effect as well as a piezoelectric pressure detector electrically connected to a measuring and display circuit of the pressure contained in that chamber, and in which the pressure contained in that chamber, and in which the Doppler effect receiver controls the display device.

The attached drawings show schematically and by way of example one embodiment of the apparatus according to the invention.

FIG. 1 is a schematic view of it.

FIG. 2 shows on a larger scale the front portion of the apparatus.

Figure 3:
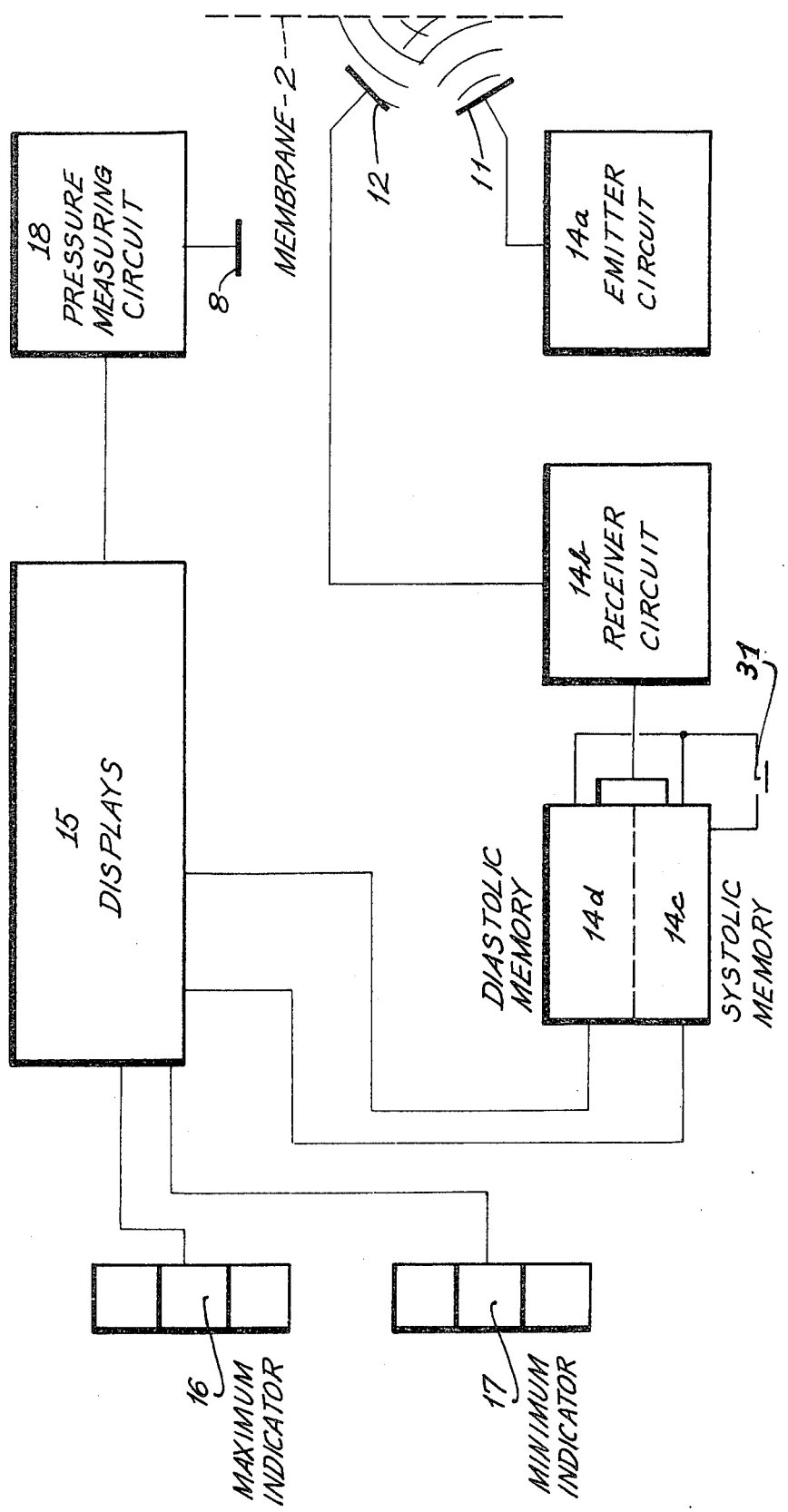
FIG. 3 is a block diagram of the apparatus.

The apparatus comprises a casing 1 the wall 2 of which is constituted by a deformable supple material. The front part of this casing comprises a measuring chamber 3 separated from the rest of the inside of the casing 1 by a wall 4. This wall 4 comprises a calibrated hole 5 as well as an aperture 6 the closing of which is controlled by a valve 7. This wall 4 carries further piezollectric pressure transducer 8 the membrane of which separates the measuring chamber 3 from the rest 9 of the casing 1.

A support 10 placed within the chamber 3 and fixed to the casing 1, carries two ultrasonic waves transducers 11, 12.

This support comprises a passageway 13 giving access from chamber 3 to transducer 8.

The transducer 11 is used as a wave emitter whilst transducer 12 is used as a detector for the ultrasonic waves which are reflected.

An emitter-receiver of ultrasonic waves 14a, 14b, electrically connected to the transducers 11 and 12, emits at a power which is lower than 200 mW/cm$^2$ in order to avoid the hemolytic effects which could be induced through the intermediary of the transducer 11.

The transducer 8 is electrically connected to a pressure measuring circuit 18 controlling a display circuit 15. This display appears however in 16 or 17 only when the presence of reflected ultrasonic waves is detected by the transducer 12. Finally a battery 19 delivers the electric power necessary to the working of the apparatus.

The resilient membrane 2 of the dome shown in full line in its rest position takes the position shown in dotted line when the operation of pressure measurement is in course, that is when this membrane 2 is applied against a member of the patient. The pressure inside the chamber 3 takes a maximum instantaneous value and diminishes slowly, due to the presence of the calibrated hole 5, the value 7 being closed.

The transducer 11 emits an ultrasonic signal which is reflected onto the transducer 12. The two transducers 11, 12 are fixed on a support 10 which permits through the apertures 13, the access of pressure to the transducer 8 used as a pressure detector. This transducer 8 has its upper part in contact with the inside of the chamber 3 and its lower part in contact with the ambient air When there is a pressure within the chamber 3, the upper part of the transducer is subjected to a mechanical stress which varies in function of the pressure. At the end of the measure and when the dome is taken away, the valve 7 is open and enables the wall 2 to resume its initial shape.

The membrane 2 of the dome deforms itself during the measurement of the pressure, and creates in the chamber 3 an instantaneous pressure which is higher than the systolic pressure to be measured. This pressure diminishes slowly due to the hole 5 and corresponds successively to the systolic and the diastolic pressures to be measured.

Thus, transducer 11 is an emitter of ultrasonic waves; while transducer 12 is a receiver of ultrasonic waves reflected by an oscillation of an arteria, the oscillation of the arteria being detected according to the known use of the Doppler effect in blood pressure measurement, as shown for example in Hochberg et al., U.S. Pat. No. 3,791,378, Feb. 12, 1974. Transducer 8 detects pressure through passage 13 and is used to measure the instantaneous pressure inside the chamber 3, according to the well known principle disclosed for example in Nakayama, U.S. Pat. No. 3,920,004, Nov. 18, 1975.

FIG. 3 shows an electrical diagram of the system used. The emitter circuit 14a is connected to the base of the emitting transducer 11; and that base emits continuously onto the membrane 2. Ultrasonic waves reflected from membrane 2 are continuously received by transducer 12 and transmitted to receiver circuit 14b. Concurrently, pressure measuring circuit 18 translates pressure variations from pressure measuring transducer 8 into electrical variations.

Receiving transducer 12 is subjected to a change in the frequency of the reflected ultrasonic emission only in the case of a vibration of the arteria. In this case, the receiver circuit 14b measures the Doppler signal obtained and actuates a systolic memory 14s in coincidence with the first reception of the Doppler effect received. This blocks the displays 15, which receive continuously the pressure information which is inside the chamber 3, via pressure measuring circuit 18. The systolic information is thus displayed in the first or maximum indicator 16. During the second phase of the Doppler effect, corresponding to the indication of diastolic pressure, the same cycle is reproduced, but the memory 14d is selected and the diastolic information is displayed in the second or minimum indicator 17. Reset to zero is effected by switch 31.

Figure 4:
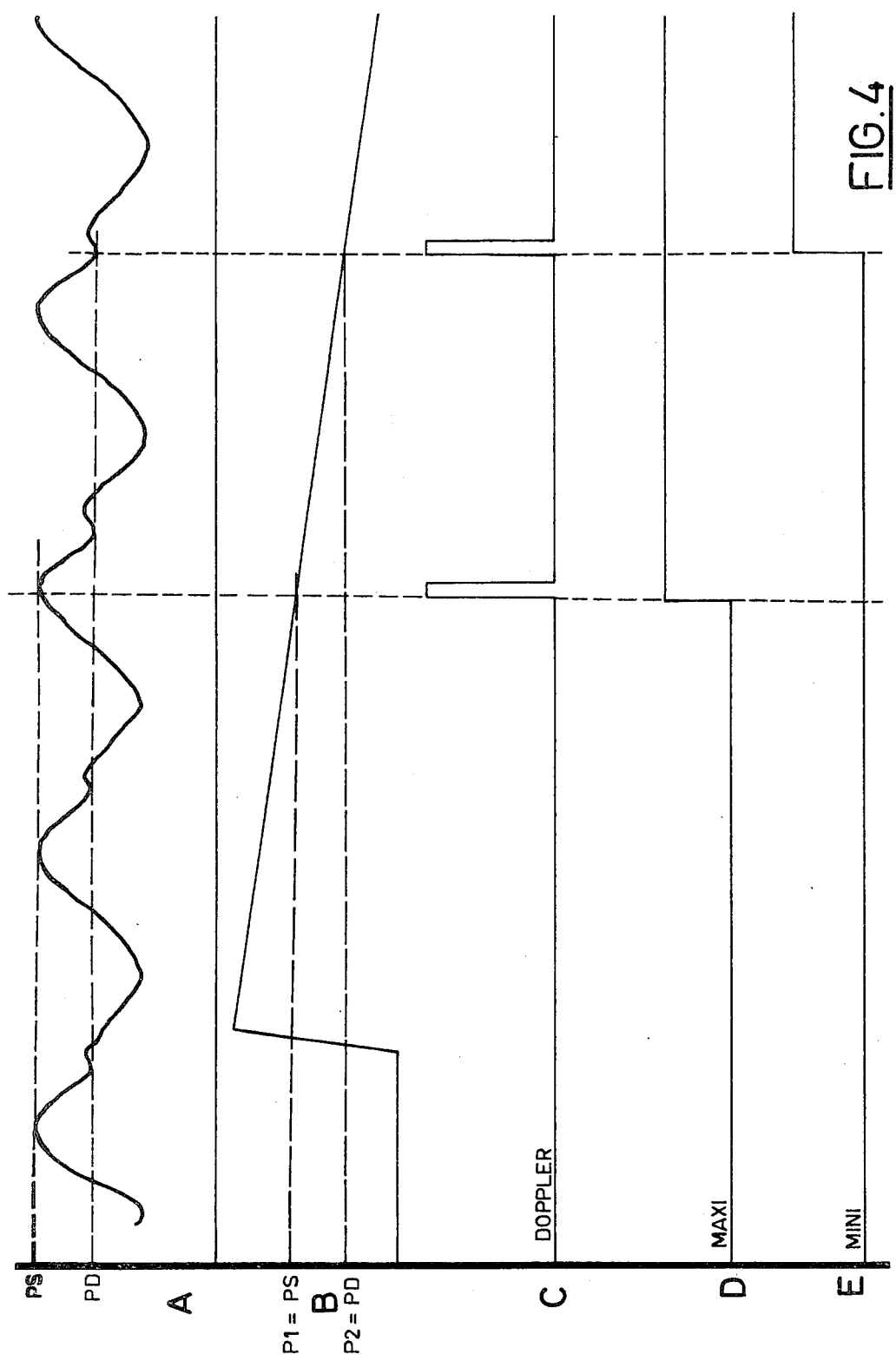
FIG. 4 shows electrical curves showing the working of the apparatus.

FIG. 4 shows electric curves of the working of the system. Curve A shows the heart beats rhythm (Ps being the systolic pressure and Pd the diastolic pressure The curve B shows the pressure within the dome before the measure and during the measure. The curve C shows the presence of Doppler effect signals in the receiver. These are defined as a function of the pressure within the dome on the one hand and as a function of the heart beat signal on the other hand. The curves D and E determine the working interval thus the blocking of the displays.

When the pressure in the chamber 3 is equal to the diastolic or systolic arterial pressure, the transducer 12 detects reflected ultrasonic waves modified by the beating of the artery. The signal which this transducer 12 delivers causes then the unlocking of the display circuit and the pressure in the chamber 3 measured by transducer 8, is displayed to the indicating circuits 16, 17 showing respectively the systolic or diastolic pressure.

The detection by the Doppler effect of the beating of an artery is already used in medicine but only in combination with a pneumatic inflatable bag permitting to apply a pressure on the arm of the patient.

Used in combination with a pressure detector of the ultrasonic waves detector, which uses the same emitter 11, this apparatus is self sufficient, and permits the direct digital reading of the arterial pressure. This apparatus is very easy and handy to use. It is to be noted that the pressure detector used is of the type of that described in Swiss Patent Application Nr. 9.857/75.

The sensitivity of this apparatus enables measurement of the arterial pressure of hypotensive individuals or of children.

I claim:

1. Automatic apparatus for the measurement of arterial pressure, comprising a housing having a supple wall at one of its ends, said wall partly defining a measuring chamber within said housing, and in said housing a piezoelectric emitter of ultrasonic waves, a piezoelectric receiver of the Doppler effect, a piezoelectric pressure detector, said emitter and receiver and detector all being spaced from said wall, a measuring and display circuit electrically connected to said pressure detector to display pressure in said chamber, said receiver controlling said display circuit, whereby when said wall is applied against the artery of a patient, the ultrasonic waves emitted by said piezoelectric emitter are reflected from said wall to said receiver and said display circuit displays the diastolic or systolic pressure of the artery to which said wall is applied, and means permitting a controlled leakage of air from said chamber.

2. Automatic apparatus as claimed in claim 1, and a further wall separating said housing into two portions one of which is said measuring chamber and the other of which contains said circuit, said emitter and detector being disposed in said measuring chamber, said pressure detector and said leakage means being carried by said further wall.

3. Automatic apparatus as claimed in claim 1, and a support within said chamber and fixed to said housing, said support carrying said emitter and said receiver, said wall and said pressure detector being disposed on opposite sides of said support, and a passageway through said support that provides communication between said pressure detector and said wall.

* * * * *